US011400304B2

(12) United States Patent
Crepin et al.

(10) Patent No.: US 11,400,304 B2
(45) Date of Patent: Aug. 2, 2022

(54) PORTABLE APPARATUS FOR GENERATING AN INDUCED LOW-FREQUENCY SINUSOIDAL ELECTRIC CURRENT

(71) Applicant: G.C. TECHNOLOGY, Aix en Provence (FR)

(72) Inventors: Gérard Crepin, Aix en Provence (FR); Patrick Meneroud, Vif (FR); Pascal Rudent, Auriol (FR)

(73) Assignee: G.C. TECHNOLOGY, Aix en Provence (FR)

( * ) Notice: Subject to any disclaimer, the term of this patent is extended or adjusted under 35 U.S.C. 154(b) by 168 days.

(21) Appl. No.: 16/762,254

(22) PCT Filed: Nov. 6, 2018

(86) PCT No.: PCT/FR2018/052728
§ 371 (c)(1),
(2) Date: May 7, 2020

(87) PCT Pub. No.: WO2019/092349
PCT Pub. Date: May 16, 2019

(65) Prior Publication Data
US 2020/0298013 A1    Sep. 24, 2020

(30) Foreign Application Priority Data
Nov. 7, 2017  (FR) ..................................... 1760443

(51) Int. Cl.
*A61N 1/40* (2006.01)
*A61N 2/12* (2006.01)

(52) U.S. Cl.
CPC ................. *A61N 1/40* (2013.01); *A61N 2/12* (2013.01)

(58) Field of Classification Search
CPC . A61N 2/00; A61N 2/02; A61N 2/004; A61N 2/12
(Continued)

(56) References Cited

U.S. PATENT DOCUMENTS 4,537,181 A * 8/1985 Shalhoob ................. A61N 2/12
600/9
5,667,469 A * 9/1997 Zhang ....................... A61N 2/12
600/9
(Continued)

FOREIGN PATENT DOCUMENTS

CN    203196141 U    9/2013
CN    203724638 U    7/2014
(Continued)

OTHER PUBLICATIONS

Office Action from corresponding Japanese Application No. 2020-544165, dated May 25, 2021.
(Continued)

*Primary Examiner* — Samuel G Gilbert
(74) *Attorney, Agent, or Firm* — Workman Nydegger

(57) ABSTRACT

A portable apparatus for generating an induced low-frequency sinusoidal electric current in an area of the human body includes four angular magnet sectors inscribed within the same circle, centered on the same axis of rotation, and spaced angularly apart from one another. The polarity of two adjacent angular magnet sectors is opposed, and a motor for rotating at a predetermined speed the angular magnet sectors is about the axis of rotation to generate an induced sinusoidal current at a predefined frequency. Each angular magnet sector includes the same geometrical shape with an internal angular opening of 90°, an external angular opening between 20° and 50°, and two lateral edges defining a radius extending over a distance, which is between one-third and two-thirds of a distance separating the axis of rotation from the free end of the magnet sectors.

12 Claims, 3 Drawing Sheets

(58) Field of Classification Search
USPC ...................................................... 600/9–15
See application file for complete search history.

(56) References Cited

U.S. PATENT DOCUMENTS

| | | | |
|---|---|---|---|
| 5,788,624 A | | 8/1998 | Lu et al. |
| 6,123,657 A | * | 9/2000 | Ishikawa .................. A61N 2/12 |
| | | | 600/9 |
| 7,560,058 B2 | | 7/2009 | Riehl et al. |
| 7,824,324 B2 | | 11/2010 | Riehl et al. |
| 7,963,903 B2 | | 6/2011 | Ghiron et al. |
| 8,246,529 B2 | | 8/2012 | Riehl et al. |
| 8,657,731 B2 | | 2/2014 | Riehl et al. |
| 9,308,386 B2 | | 4/2016 | Riehl et al. |
| 9,931,518 B2 | | 4/2018 | Riehl et al. |
| 10,617,884 B2 | | 4/2020 | Riehl et al. |
| 2007/0027353 A1 | | 2/2007 | Ghiron et al. |
| 2007/0027354 A1 | | 2/2007 | Riehl et al. |
| 2007/0027355 A1 | | 2/2007 | Riehl et al. |
| 2008/0081940 A1 | | 4/2008 | Byun |
| 2009/0240096 A1 | | 9/2009 | Riehl et al. |
| 2009/0247808 A1 | | 10/2009 | Riehl et al. |
| 2011/0015464 A1 | | 1/2011 | Riehl et al. |
| 2011/0237861 A1 | | 9/2011 | Pool et al. |
| 2012/0010454 A1 | | 1/2012 | Lamb |
| 2014/0163305 A1 | | 6/2014 | Watterson |
| 2016/0303393 A1 | | 10/2016 | Riehl et al. |
| 2018/0178026 A1 | | 6/2018 | Riehl et al. |

FOREIGN PATENT DOCUMENTS

| | | |
|---|---|---|
| DE | 4132078 A1 | 4/1993 |
| JP | 60016181 A | 1/1985 |
| JP | S63181777 A | 7/1988 |
| JP | S63181777 U | 11/1988 |
| JP | H09502623 A | 3/1997 |
| JP | 2001313205 A | 11/2001 |
| JP | 2008068056 A | 3/2008 |
| JP | 2011004786 A | 1/2011 |
| JP | 2016029998 A | 3/2016 |
| JP | 2016144757 A | 8/2016 |
| WO | 2008014902 A1 | 2/2008 |

OTHER PUBLICATIONS

Search Report from corresponding FR Application No. FR1760443, dated Jun. 6, 2018.
International Search Report and Written Opinion from PCT Application No. PCT/FR2018/052728, dated Jan. 4, 2019.

* cited by examiner

PORTABLE APPARATUS FOR GENERATING AN INDUCED LOW-FREQUENCY SINUSOIDAL ELECTRIC CURRENT

BACKGROUND OF THE INVENTION

The present invention relates to the general field of magnetic therapy, and particularly to portable apparatuses which generate an induced low-frequency sinusoidal electric current intended to be applied to an area of the human body with the aim of exerting an analgesic and anti-inflammatory action.

In a known manner, to generate an induced electric current, magnetic therapy uses a variable magnetic field, particularly to relieve articular and periarticular pain, this variable magnetic field being created by a magnetic source, a coil or a magnet. In the case of magnets, these latter are set in motion to create the induced current.

Magnetic therapy is generally implemented using an apparatus (usually portable) displaced at the level of the area of the body to be treated, this apparatus enclosing magnets, for example rotary magnets, and a motor to allow these magnets to generate a variable magnetic field inducing an electric field proportional to the speed of the variation (Faraday's law).

Thus, from the document WO 2008/014902 there is known a portable apparatus for generating a sinusoidal magnetic field for therapeutic purposes, this apparatus comprising four angular magnet sectors which are flat, of the same geometrical shape, centered on one and the same axis of rotation and angularly spaced apart from one another, the polarity of two adjacent angular magnet sectors being opposite. Thus disposed, the angular magnet sectors are rotationally driven by a motor in order to generate a sinusoidal magnetic field at a predefined frequency.

It is moreover known that the therapeutic effect obtained is linked to the electrical currents induced by the rotation of the angular magnet sectors, on condition that the amperage of these currents exceeds a certain threshold. It is also known that the induced currents are proportional to the speed of linear displacement of the magnets. However, for a given rotation speed, the speed of linear displacement is greater at the end of the angular magnet sectors than at the level of their axis of rotation. In addition, to obtain a sinusoidal magnetic field with the apparatus described in the document WO 2008/014902, it is necessary to use magnets in the shape of angular sectors, which further reduces the magnetic field at the center of the apparatus.

Also, the apparatus described in the document WO 2008/014902 has the drawback that the amperage of the electric currents induced at the level of the center of the apparatus does not exceed the threshold necessary for the obtainment of a therapeutic effect. However, the center of the apparatus is typically the area the most heavily used by the user of the apparatus. This is because, naturally, the user tends to center the apparatus on the pain or pathology to be treated.

Another drawback of the apparatus described in this document is that the space between the magnets generates a signal with a double peak in an area near the surface of the apparatus, and therefore a high rate of harmonic distortion.

Moreover, the therapeutic effects of such an apparatus being obtained for very low frequencies, preferably less than 10 Hz, it is not desirable to increase the field $\vec{V} \times \vec{B}$ by increasing the rotation speed of the magnets. Specifically, this increase in the field $\vec{V} \times \vec{B}$ would have the consequence of reducing the therapeutic effects obtained.

SUBJECT AND SUMMARY OF THE INVENTION

The present invention therefore has the main goal of overcoming such drawbacks by proposing an apparatus that makes it possible to generate an induced low-frequency sinusoidal electric current, the amperage of which exceeds a predefined threshold over the entire surface covered by the apparatus.

This goal is achieved owing to a portable apparatus for generating an induced low-frequency sinusoidal electric current in an area of the human body, the apparatus comprising four angular magnet sectors of the same geometrical shape, centered on one and the same axis of rotation and angularly spaced apart from one another, the polarity of two adjacent angular magnet sectors being opposite, and means for setting in rotation at a predetermined speed the angular magnet sectors about the axis of rotation such as to generate an induced sinusoidal current at a predefined frequency, an apparatus in which, in accordance with the invention, each angular magnet sector comprises an internal angular opening at the level of the axis of rotation of 90°, an external angular opening at the level of a free end opposite the axis of rotation between 20° and 50°, and two lateral edges defining a radius extending over a distance which is between one-third and two-thirds of a distance separating the axis of rotation from the free end of the angular magnet sectors.

The inventors have discovered that the particular shape of the angular magnet sectors with an internal angular opening at the level of the axis of rotation of 90°, an external angular opening at the level of a free end opposite the axis of rotation between 20° and 50° (and preferably equal to 45°), and two lateral edges defining a radius extending over a distance which is between one-third and two-thirds of a distance separating the axis of rotation from the free end of the angular magnet sectors makes it possible to obtain a sinusoidal magnetic field the intensity of which is homogenous and above a predefined threshold between the axis of rotation and the free end of the angular magnet sectors.

In particular, it has been found that this arrangement of the angular magnet sectors makes it possible to obtain an increase in the order of 70% in the intensity of the sinusoidal magnetic field at the level of the center of the apparatus compared with the apparatus described in the document WO 2008/014902. It has also been observed that the inhomogeneity of the magnetic field over the whole surface of the apparatus is reduced by over 35% compared with the apparatus of the document WO 2008/014902. Finally, the particular shape of the angular magnet sectors makes it possible to reduce the rate of harmonic distortion (up to 25% compared with the shape of the magnet sectors described in the document WO 2008/014902).

In an embodiment, the distance separating the axis of rotation from the free end of each angular magnet sector is 60 mm, the join radius defined by the lateral edges of the angular magnet sectors being 40 mm.

The angular magnet sectors can possess a substantially constant thickness. In this case, the angular magnet sectors preferably possess a thickness between 2 mm and 15 mm.

Alternatively, the angular magnet sectors can possess a thickness that is variable between the axis of rotation and their free end. In this case, the thickness of the angular magnet sectors is preferably decreasing from the axis of rotation between a maximum thickness and a minimum thickness. In addition, each angular magnet sector has a rear face substantially perpendicular to the axis of rotation and a front face opposite the rear face which is inclined with respect to the rear face.

Also preferably, the apparatus further comprises a magnetic circuit layer disposed on the back of the angular magnet sectors. This magnetic circuit layer can be made of soft steel.

The presence of this magnetic circuit layer on the back of the angular magnet sectors makes it possible to reduce the charge of these latter and to increase the magnetic field that they generate. In addition, the magnet surface facing the treatment area is modified by increasing the relative proportion of magnet over small radii (in order to increase the magnetic field source over these small radii) and by reducing the surface over the largest radii, which makes the induced magnetic field more homogenous between the axis of rotation and the free end of the angular magnet sectors.

Also preferably, the apparatus further comprises a magnetic shielding layer disposed about the angular magnet sectors. This magnetic shielding layer, which can be made of nickel-iron alloy, makes it possible to greatly limit the radiation of the induced magnetic field at the rear and on the sides of the apparatus.

BRIEF DESCRIPTION OF THE DRAWINGS

Other features and advantages of the present invention will become apparent from the description given below, with reference to the appended drawings which illustrate an exemplary embodiment thereof devoid of any limiting character. In the figures.

DETAILED DESCRIPTION OF THE INVENTION

Figure 1:
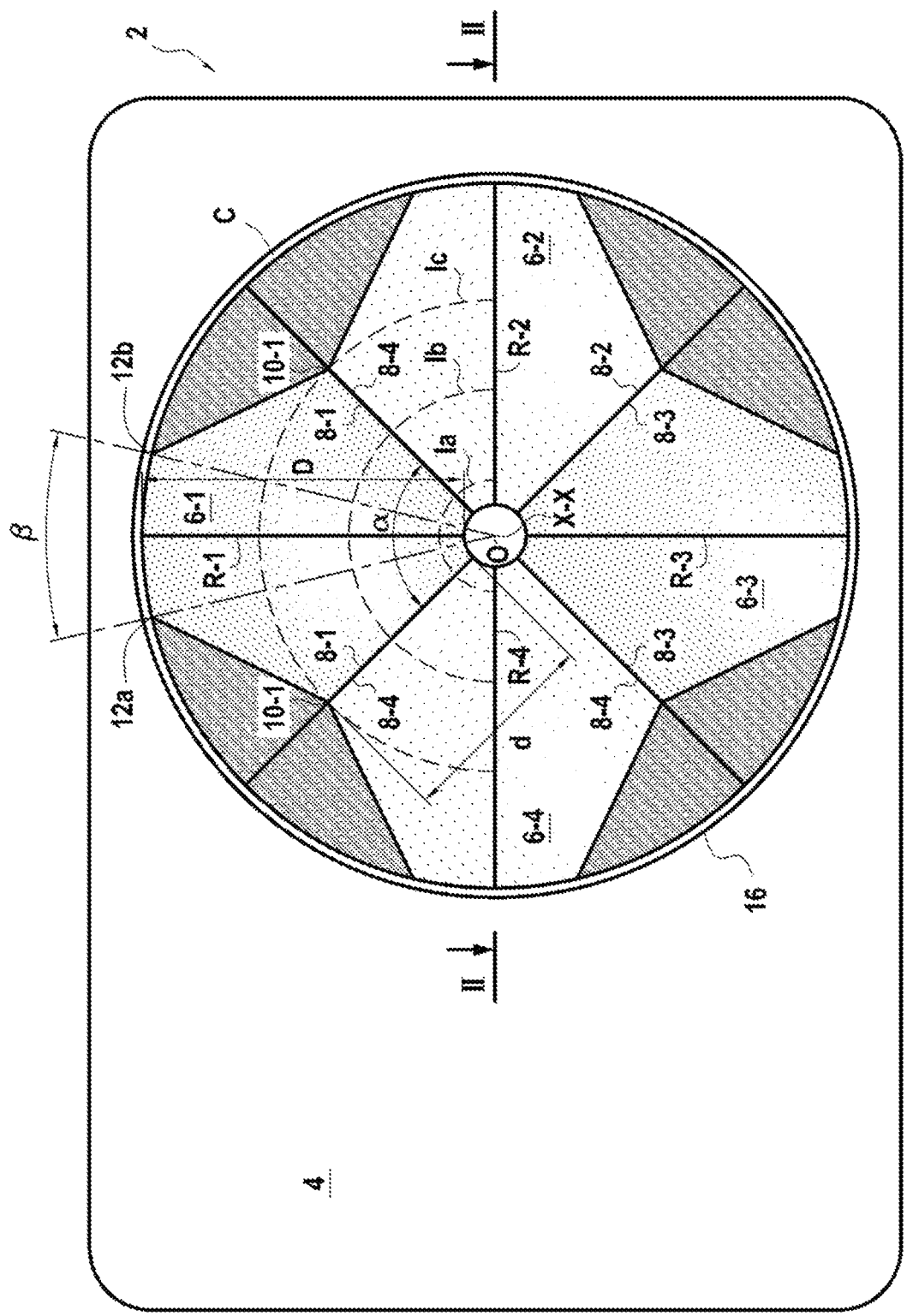
FIG. 1 is a schematic view of an apparatus according to an embodiment of the invention.
Figure 2:
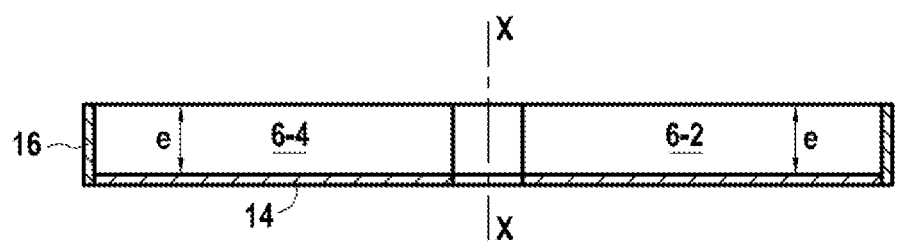
FIG. 2 is a section view along II-II of FIG. 1.

FIGS. 1 and 2 schematically represent a portable apparatus 2 according to the invention for generating an induced low-frequency sinusoidal electric current intended to be applied to an area of the human body.

This apparatus 2 comprises a casing 4 inside which are assembled four angular magnet sectors 6-1 to 6-4 having one and the same geometrical shape and centered on one and the same axis of rotation X-X. These four angular magnet sectors 6-1 to 6-4 are contained inside a circle C of diameter D and of center O.

More precisely, the angular magnet sectors 6-1 to 6-4 are angularly spaced apart from one another about the axis of rotation X-X and are disposed such that the polarity (North or South) of two adjacent angular magnet sectors is opposite. In other words, two angular magnet sectors which are diametrically opposed have the same polarity.

Thus, on the example represented in FIGS. 1 and 2, the angular magnet sectors 6-1 and 6-3 have a polarity N, whereas the angular magnet sectors 6-2 and 6-4 have a polarity S.

The angular magnet sectors are typically made of rare earth magnet (such as Neodymium Iron Boron), the features of which are a remanent magnetization ranging from 0.83 T to 1.47 T and an energy density (BH)max ranging from 135 kJ/m$^3$ to 415 kJ/m$^3$.

The apparatus 2 further comprises means for setting in rotation the four angular magnet sectors 6-1 to 6-4 about the axis of rotation X-X.

In an exemplary embodiment, these means appear in the form of an electric motor and a belt drive. Of course, any other means could be envisioned to provide this setting in rotation.

According to the invention, the four angular magnet sectors 6-1 to 6-4 each have a shape that is symmetrical with respect to a radius of symmetry R-1 to R-4, respectively, of the circle C inside which they are contained.

Each angular magnet sector 6-1 to 6-4 comprises two lateral edges 8-1 to 8-4 which are symmetrical with respect to the radius of symmetry of the angular magnet sector and which are facing or in direct contact with corresponding lateral edges of two adjacent angular magnet sectors.

In addition, the two lateral edges 8-1 to 8-4 of each angular magnet sector define a join radius (delimited between the center O of the circle C and the point 10-1 to 10-4 of the lateral edge furthest from the center O) which extends over a distance d corresponding to two-thirds of the radius D/2 of the circle C (i.e. to two thirds of the distance separating the axis of rotation X-X from the free end of the angular magnet sectors). For reasons of convenience, only the points 10-1 of the angular magnet sector 6-1 are represented in FIG. 1.

Thus, in an exemplary embodiment for which the angular magnet sectors are contained in a circle C of 120 mm in diameter D, the distance d over which extend the join radii defined by the lateral edges of the angular magnet sectors is 40 mm.

Furthermore, the lateral edges 8-1 to 8-4 of each angular magnet sector form between them an angle α of 90° (it is also said that the internal angular opening α of each angular magnet sector at the level of the axis of rotation X-X is of) 90°.

Still according to the invention, each angular magnet sector further comprises an external angular opening β at the level of one free end opposite the axis of rotation X-X which is between 20° and 50°, and preferably equal to 45°.

In other words, the free end of each angular magnet sector 6-1 to 6-4 is delimited between two points 12a, 12b located on the circle C in which the angular magnet sectors are contained. These points are symmetrical and the radii formed by the points O and 12a, on the one hand, and O and 12b, on the other hand, form between them an angle β between 20° and 50°, and preferably equal to 45°.

For reasons of convenience, only the points 12a, 12b and the angle β of the angular opening relating to the angular magnet sector 6-1 are represented in FIG. 1. Of course, the same features also apply to the other angular magnet sectors 6-2 to 6-4.

The described general configuration of the angular magnet sectors of the apparatus according to the invention thus has a star shape contained in the circle C of center O.

The angular magnet sectors 6-1 to 6-4 of the apparatus according to the invention are set in rotation about the axis of rotation X-X at a preferable speed of 300 revolutions per minute, which generates an induced sinusoidal electric current at a frequency preferably less than or equal to 10 Hz.

Figure 3:
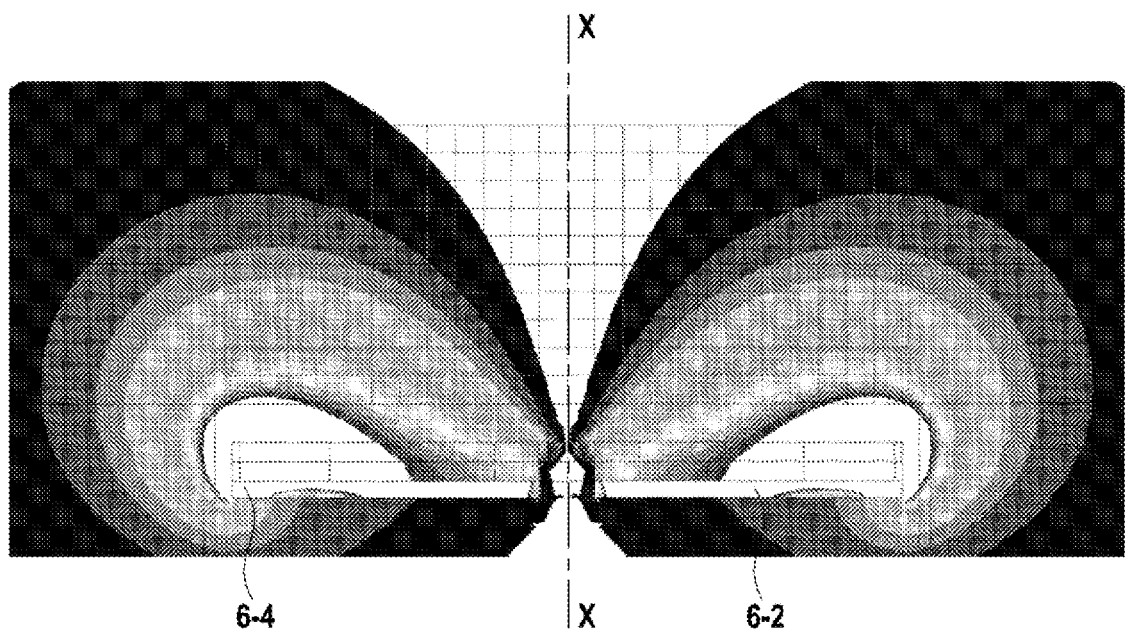
FIG. 3 shows the distribution of the induced field $\vec{V} \times \vec{B}$ obtained by the apparatus of FIG. 1.

FIG. 3 shows the spatial distribution of the induced field $\vec{V} \times \vec{B}$ (V being the speed field and B the magnetic induction field) obtained by the apparatus according to the invention when the angular magnet sectors are set in rotation at a speed of 300 revolutions per minute. This distribution is illustrated in a plane median to the angular magnet sectors.

This distribution shows that the induced field $\vec{V} \times \vec{B}$ has an intensity exceeding a predefined threshold over the entire surface covered by the apparatus.

This FIG. 3 also makes it possible to show that the particular disposition and shape of the angular magnet sectors according to the invention significantly increases (in the order of 70%) the intensity of the induced magnetic field near the axis or over low radii compared with angular magnet sectors having a shape as disclosed in the document WO 2008/014902).

Figure 4:
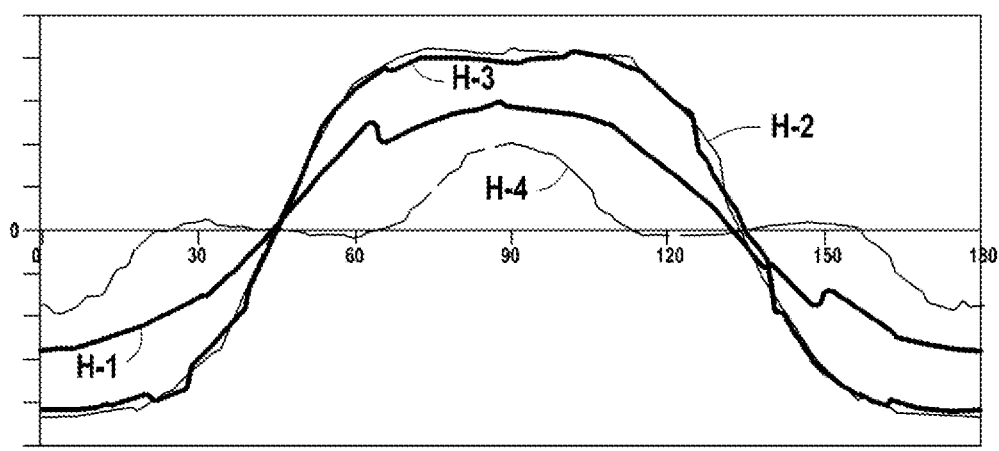
FIG. 4 shows induction curves obtained by the apparatus of FIG. 1 over different radii.

FIG. 4 illustrates different curves of the vertical component of induction obtained by the apparatus according to the invention over different radii of the circle in which the angular magnet sectors are contained.

Thus, the curve H-1 illustrates the vertical component (i.e. along the axis of rotation X-X) of the induction generated at the level of the radius Ia represented in FIG. 1, the curve H-2 illustrates that generated at the level of the radius Ib, the curve H-3 illustrates that generated at the level of the radius Ic, and the curve H-4 illustrates that generated at the level of the radius D/2 of the circle C. On these curves, the vertical component of the induction is measured in microtesla and the angle of the radius in degrees.

These curves show that the distribution of the generated induction is relatively homogenous over the whole surface of the apparatus. In particular, the inhomogeneity of the magnetic field over the whole surface of the apparatus is reduced by over 35% compared with the apparatus of the document WO 2008/014902.

Figure 5:
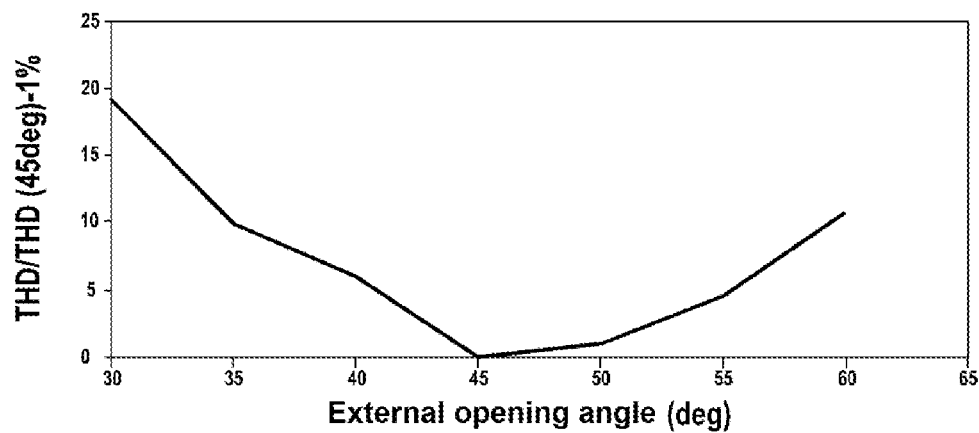
FIG. 5 shows the variation in the rate of harmonic distortion as a function of the angle of the external angular opening.

FIG. 5 illustrates the variation of the rate of harmonic distortion (THD) as a function of the value of the angle β of the external angular opening of the angular magnet sectors. This figure shows that the rate of harmonic distortion is lower for an angle β of the external angular opening equal to approximately 45°.

Figure 6:
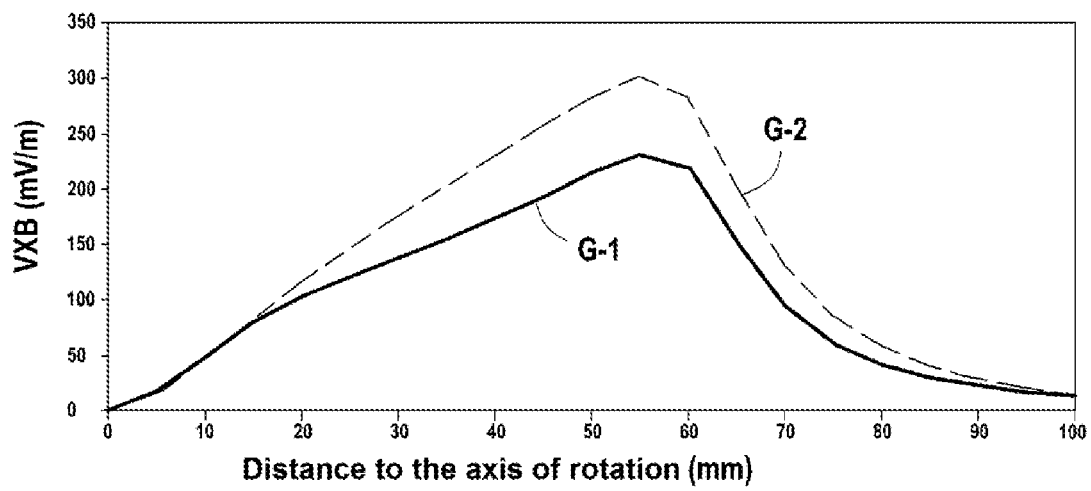
FIG. 6 represents curves of comparison of the field distribution with respect to the distance to the axis of rotation between the apparatus according to the invention and an apparatus according to the prior art.

FIG. 6 represents curves G-1, G-2 of the field distribution $\vec{V} \times \vec{B}$ (in mV/m) as a function of the distance to the axis of rotation X-X for the apparatus according to the invention (curve G-1) and for an apparatus according to the prior art of the type described in the publication WO WO 2008/014902 (curve G-2). More precisely, these curves have been produced with an apparatus according to the invention in which the angular magnet sectors have a constant thickness of 4.2 mm for a total weight of 393 g, whereas the magnet sectors of the apparatus according to the prior art have a constant thickness of 10 mm for a total weight of 432 g.

It can be seen on this figure that a better homogeneity of distribution of the field is obtained by the apparatus according to the invention. In particular, the apparatus according to the invention allows a gain of 38% between the maximum and the minimum of the field with respect to an apparatus according to the prior art. In addition, the apparatus according to the invention allows a gain compared with an apparatus according to the prior art of 25% of the field at a distance of 5 mm from the axis of rotation of the angular magnet sectors. Finally, these gains are obtained with a reduction of 58% of the thickness of the magnets and a decrease in 9% of their total mass.

Moreover, in the embodiment of FIGS. 1 and 2, the angular magnet sectors 6-1 to 6-4 each possess one and the same thickness e which is substantially constant (the angular magnet sectors are flat). Preferably, for angular magnet sectors contained in a circle C of 120 mm in diameter, this thickness e is between 2 mm and 10 mm.

Figure 7:
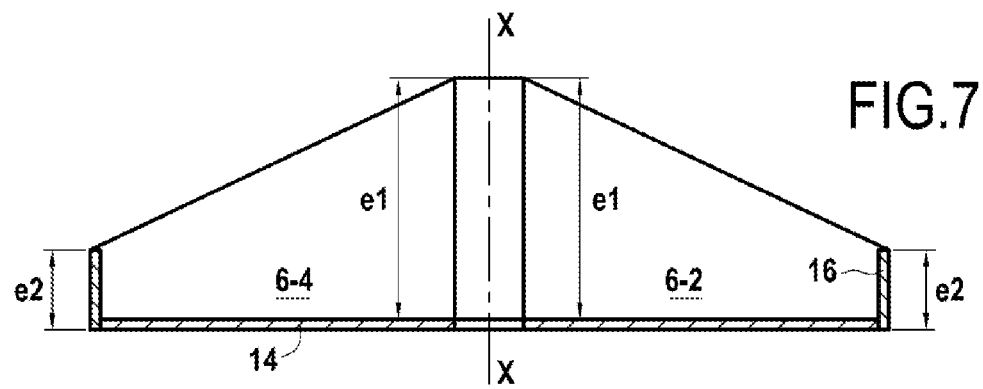
FIG. 7 is a schematic section view showing an apparatus according to a variant embodiment of the invention.

In a variant embodiment represented in FIG. 7, the angular magnet sectors each possess a thickness which is variable between the axis of rotation X-X and their free end.

More precisely, this thickness is decreasing from the axis of rotation with a maximum thickness e1 and a minimum thickness e2, the maximum thickness e1 being between 2 and 5 times the minimum thickness e2.

Thus, the thickness of the angular magnet sectors is decreasing from the axis of rotation between the maximum thickness e1 and the minimum thickness e2. In other words, each angular magnet sector has a rear face (i.e. opposite the treatment area) substantially perpendicular to the axis of rotation X-X and a front face (turned toward the treatment area) opposite the rear face which is inclined with respect to the rear face.

Compared with a flat shape, the beveled shape of the angular magnet sectors makes it possible, on the one hand, to further increase the intensity of the induced magnetic field at the level of the center of the apparatus, and on the other hand to further reduce the rate of harmonic distortion.

There will now follow a description of different advantageous features of the apparatus according to the invention which apply to the two embodiments previously described.

As represented in FIG. 2, the apparatus advantageously comprises a magnetic circuit layer 14 which is disposed on the back of the angular magnet sectors 6-1 to 6-4 (i.e. on the side of the face of the angular magnet sectors which is opposite that turned toward the treatment area to be treated).

For example, the magnetic circuit layer is a layer of soft steel of constant thickness which covers the entire surface of the angular magnet sectors.

It has been remarked that the present of this magnetic circuit layer makes it possible to reduce the charge of the angular magnet sectors and to increase the magnetic field that they generate. In addition, the magnet surface facing the treatment area is modified by increasing the relative proportion of magnet over small radii (in order to increase the magnetic field source over these small radii) and by reducing the surface over the largest radii, which makes the induced max more homogenous between the axis of rotation and the free end of the angular magnet sectors.

According to another advantageous disposition represented in FIG. 1, the apparatus further comprises a magnetic shielding layer 16 which is disposed about the angular magnet sectors (i.e. along the circumference of the circle C in which these latter are contained). For example, the magnetic shielding layer of a thickness between 0.1 mm and 2 mm is made of mu-metal (i.e. of nickel and iron alloy).

The invention claimed is:

1. A portable apparatus for generating an induced low-frequency sinusoidal electric current in an area of a human body, the apparatus comprising:
    four angular magnet sectors which are inscribed in within a same circle, are centered on an axis of rotation and spaced angularly apart from one another, the polarity of two adjacent angular magnet sectors being opposed; and means for rotating the angular magnet sectors at a predetermined speed about the axis of rotation such as to generate an induced sinusoidal current at a predefined frequency;

wherein each said angular magnet sector comprises a same geometrical shape with an internal angular opening at a level of the axis of rotation of 90°, an external angular opening at a level of a free end opposite the axis of rotation between 20° and 50°, and two lateral edges defining a radius extending by a distance which is between one-third and two-thirds of a distance separating the axis of rotation from the free end of the angular magnet sectors.

2. The apparatus according to claim 1, wherein the external angular opening of each said angular magnet sector is 45°.

3. The apparatus according to claim 1, wherein the distance separating the axis of rotation from the free end of each said angular magnetic sector is 60 mm, a join radius defined by the lateral edges of the angular magnet sectors extending over a distance of 40 mm.

4. The apparatus according to claim 1, wherein the angular magnet sectors have a substantially constant thickness.

5. The apparatus according to claim 4, wherein the angular magnet sectors have a thickness between 2 mm and 15 mm.

6. The apparatus according to claim 1, wherein the angular magnet sectors have a thickness that is variable between the axis of rotation and the free end thereof.

7. The apparatus according to claim 6, wherein the thickness of the angular magnet sectors is decreasing from the axis of rotation between a maximum thickness and a minimum thickness.

8. The apparatus according to claim 7, wherein each said angular magnet sector has a rear face substantially perpendicular to the axis of rotation and a front face opposite the rear face which is inclined with respect to the rear face.

9. The apparatus according to claim 1, further comprising a magnetic circuit layer disposed on a back of the angular magnet sectors.

10. The apparatus according to claim 9, wherein the magnetic circuit layer is made of soft steel.

11. The apparatus according to claim 1, further comprising a magnetic shielding layer disposed around the angular magnet sectors.

12. The apparatus according to claim 11, wherein the magnetic shielding layer is made of nickel-iron alloy.

* * * * *